United States Patent [19]

Davenport et al.

[11] Patent Number: 4,612,094

[45] Date of Patent: Sep. 16, 1986

[54] ELECTRICAL CONDITIONING OF A PLATINUM ELECTRODE USEFUL IN MEASUREMENT IN HYPOCHLORITE

[75] Inventors: James W. Davenport, Lake Jackson, Tex.; Thomas H. Perry, Jr., Dalton, Ga.

[73] Assignee: The Dow Chemical Company, Midland, Mich.

[21] Appl. No.: 762,224

[22] Filed: Aug. 5, 1985

[51] Int. Cl.$^4$ ................................................ C25F 1/04
[52] U.S. Cl. .................................................... 204/141.5
[58] Field of Search ...................................... 204/141.5

[56] References Cited

U.S. PATENT DOCUMENTS

| Re. 28,849 | 6/1976 | Itai | 204/129.75 |
| 3,030,286 | 4/1962 | Tao | 204/141.5 |
| 3,213,004 | 10/1965 | Schmidt | 204/144.5 |
| 3,574,074 | 4/1971 | Khera | 204/140 |

Primary Examiner—T. M. Tufariello
Attorney, Agent, or Firm—James H. Dickerson

[57] ABSTRACT

The present disclosure sets forth improvements in a cleaning procedure to clean electrodes exposed to hypochlorite in a measuring device. Typical measuring electrodes are made of platinum, gold, silver or other conductive metals. The electrode is dipped in a strong acid bath, a sacrificial oxide coated titanium electrode is placed in the bath and a DC power source is connected between the metal electrode requiring protection and the sacrificial electrode to create current flow until the surface has been treated. Current flow accomplishes the treatment after which the electrode can be removed and used in measuring hypochlorite concentration.

12 Claims, 1 Drawing Figure

U.S. Patent Sep. 16, 1986 4,612,094
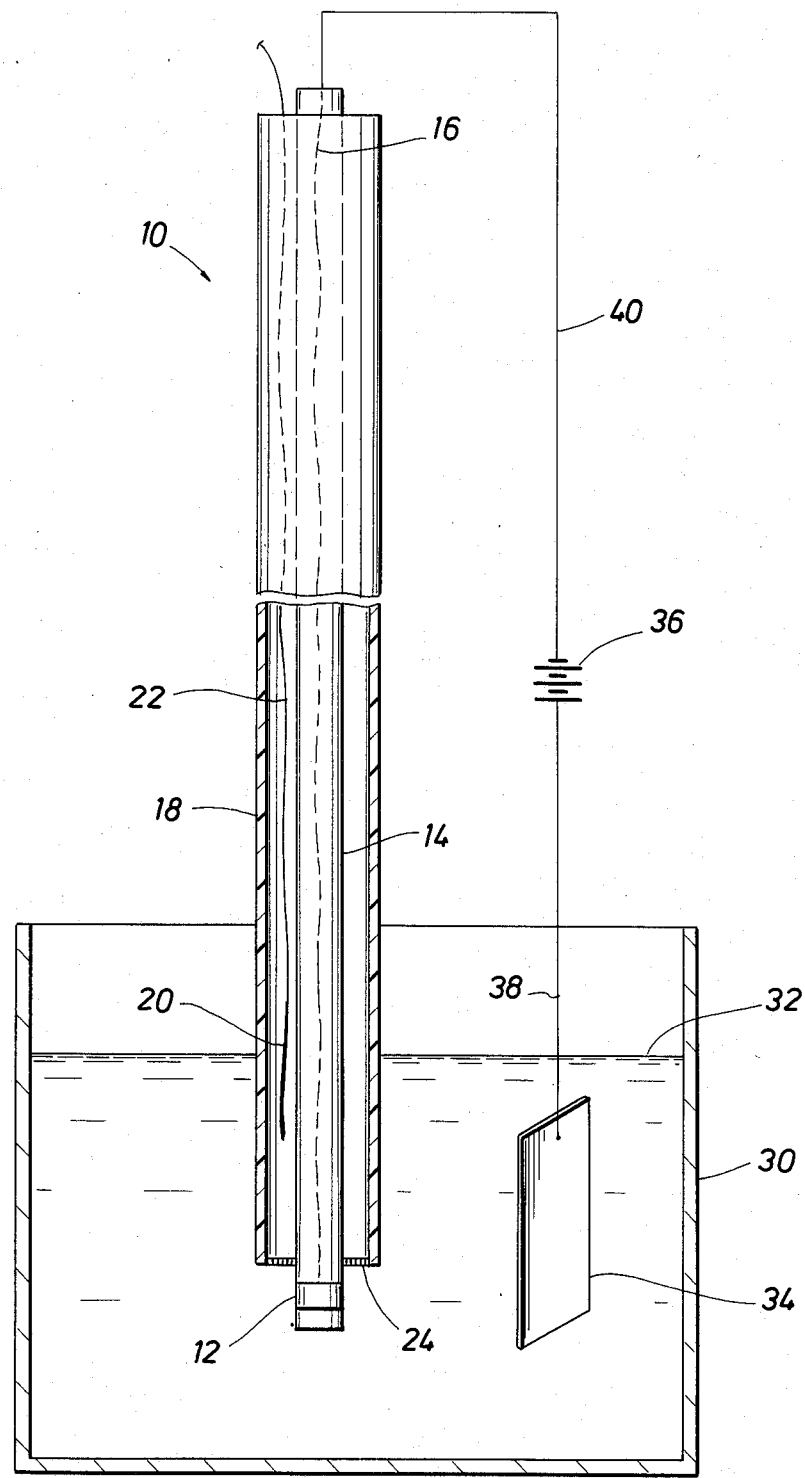

4,612,094

ELECTRICAL CONDITIONING OF A PLATINUM ELECTRODE USEFUL IN MEASUREMENT IN HYPOCHLORITE

BACKGROUND OF THE DISCLOSURE

In electrochemical cells using current flow through a diaphragm in the cell, holes in the diaphragm are indicated by increase in the concentration of hypochlorite in the vicinity of the cathode. An apparatus for measuring hypochlorite concentration in the catholyte is described in copending application Ser. No. 762,225 of the common assignee of the present disclosure. Such a measurement system utilizes a pair of dissimilar metal electrodes, the preferred embodiment utilizes a platinum electrode whch is exposed to the hypochlorite in the catholyte. The catholyte solution is strongly basic, (usually NaOH), and the electrode thus ultimately forms a film over the surface as a result of exposure to the strong basic catholyte. The preferred electrode material is platinum but it will be understood that other noble metals can also be used.

The procedure of the present disclosure sets forth a method of cleaning the exposed electrode. Even though the electrode is a noble metal that does not easily oxidize, it does nevertheless on exposure to strong basic catholyte form a surface film which might be described as an oxidation film. Ultimately, this film interferes with the function of the electrode. This is especially important because the sensitivity of the measurement system depends in large part on having clean electrode surfaces, meaning surfaces free of film or other deposits thereon.

The present procedure cleans such a surface, and particularly restores the surface to a bright metal condition substantially free of surface film. The procedure is successful with noble metals other then platinum including gold and silver. It is particularly able to cleanse electrodes which have been exposed to strong basic solutions forming the film on the electrodes. It is believed to be successful for electrodes of any shape provided they can be exposed to the process described below and connected in a circuit as will be described.

One reference of interest is U.S. Pat. No. 3,030,286. This is directed to descalling titanium alloy articles. U.S. Pat. No. RE28,849 is a surface preparation process utilizing various strong acids. U.S. Pat. No. 3,574,074 discloses an AC current system using a strong acid. As will be more readily apparent upon consideration of the specification below, there are a number of factors wherein the hypochlorite measuring electrodes of the present disclosure are dressed and prepared for accuracy or repetition in operation by the treatment herein disclosed. References is made to the specification and the drawings described below.

BRIEF DESCRIPTION OF THE DRAWINGS

So that the manner in which the above-recited features, advantages and objects of the present invention, as well as others which will become apparent, are attained and can be understood in detail, a more particular description of the invention, briefly summarized above, may be had by reference to the embodiment thereof illustrated in the appended drawings, which drawings form a part of this specification.

It is to be noted, however, that the appended drawings illustrate only typical embodiments of this invention and are not to be considered limiting of its scope, for the invention may admit to other equally effective embodiments.

The single drawings shows an electrode assembly especially useful in measurement of hypochlorite concentration in a strong basic catholyte momentarily placed in an acid solution and connected with a sacrifical electrode for cleaning to thereby yield high repeatability.

DETAILED DESCRIPTION OF THE PREFERRED EMBODIMENT

Attention is first directed to the only drawing which is incorporated herewith where the numeral 10 identifies an electrode assembly used in measurement of hypochlorite concentration. The electrode assembly is incorporated within a structure comprising a measurement gun particularly useful for measurement of hypochlorite concentration in strong basic catholyte solutions typically found in electrochemical processing cells. Moreover, the measurement gun that utilizes the electrode assembly shown in this disclosure is better set forth in application Ser. No. 762,225. It features the electrode assembly 10 which has been shown in the single drawing herewith and which is otherwise incorporated in a measurement gun structure for easy hand application. Accordingly, the electrode assembly 10 will be first described and the method of treatment will be described thereafter. A platinum ring like electrode 12 is supported on an elongate sealed tubular member 14. The tubular member 14 has a lower end portion where the platinum ring is supported. The platinum ring is supported on the seal member 14. The member 14 encloses a conductor 16 which extends to the top end of the equipment for the connection with other components. The elongate sealed member 14 is typically formed of glass or other materials not harmed by exposure to strong basic catholyte.

A larger cylindrical member 18 encompasses the member 14 to define an annular space therebetween. In the annular space, a second electrode 20 is located. The electrode 20 is silver plated with silver chloride. The electrode 20 is connected to a conductor 22 which extends from the apparatus, the conductors 16 and 22 enabling connection of the dissimilar electrodes to a voltage measuring device such as a volt meter.

The annular space within the cylindrical housing 18 is filled with a conductive gel. An alternative is a liquid, differing primarily from the gel in viscosity. The gel surrounds and contacts the electrode 20. The gel is located above a glass frit 24. The glass frit enables any solution surrounding the lower end electrode to electrically contact the conductive gel above the frit thereby establishing a current conductive path between the electrodes 12 and 20. Thus, the current path must flow through the solution and into the conductive gel. The serial path thus incorporates the solution which is tested by the dissimilar electrode assembly shown at 10.

After use for a period of time, the platinum electrode 12 accumulates a film. While the film might be a thin layer of oxide, nevertheless, the film is accumulated on exposure repetitively to strong basic catholyte solutions in measurement of hypochlorite concentration. This film destroys linear performance of the system. It coats the platinum electrode 12 and thereby creates error in measurement. Accordingly, the electrode assembly is momentarily treated as will be described. The electrical preconditioning to assure measurement accuracy utilizes a container 30 which is filled with an aqueous acid bath. A suitable acid bath is about four normal $H_2SO_4$. The bath is indicated at 32. A sacrificial electrode 34 is placed in the bath. An acceptable electrode is titanium having a coating of RuO. This electrode is placed in the bath 32, and is connected with a battery or other DC power source 36. The electrode conductor is identified at 38, and the remaining battery conductor 40 is then connected to the platinum conductor 16. This completes the circuit. In other words, the positive terminal of the battery is connected with the titanium electrode and the negative terminal of the battery is connected with a platinum electrode to be cleaned.

The electrodes in the bath 32 are spaced apart by some suitable distance usually as at least 2 or 3 inches apart, and the voltage of the source is then increased to provide current flow between the two electrodes in the bath. A suitable voltage is determined to provide a current flow of about 10 ma which is then permitted to flow for about 3 minutes. After this interval, the battery can be removed and the electrode assembly 10 can then be restored to its usual operation and use. Moreover, the platinum electrode at this juncture has been cleaned and its exposed surface is chemically stablized by removal of film or other oxides deposited on it. This is particularly useful pretreatment prior to placing the electrode assembly 10 in strong basic catholyte solutions.

After the pretreatment described above, hypochlorite measurement is extremely accurate as a result of surface cleansing at the platinum electrode. It is particularly important to note that the platinum electrode is exposed to strong basic catholytes which tend to attack the platinum electrode thereby forming thin films on the platinum electrode. The cleaning of the electrode enables more reliable measurements to be obtained by the dissimilar pair of electrodes in the electrode assembly 10. This system can be used to clean the platinum electrode periodically. It is conveniently implemented, requires only a few minutes, and the electrode cleaning process can be used repeatedly until depletion of the strong acid bath or the titanium electrode. The electrode 36 is a sacrificial device, and is therefore used until replacement is required.

While the foregoing is directed to the preferred embodiment, the scope thereof is determined by the claims which follow.

What is claimed is:

1. A method of preconditioning corrosion resistant electrodes made of platinum, gold, silver, or noble metals and subject to forming a film thereon resulting from use; the method comprising the preuse, pretreatment steps of:
   (a) immersing the electrode in an acid bath before use;
   (b) additionally placing a sacrificial oxide coated titanium electrode in the bath;
   (c) connecting a DC power source to the electrode and also the titanium electrode wherein the power source is connected such that the negative terminal thereof connects to the metal electrode and the titanium electrode is connected to the positive terminal thereof; and
   (d) adjusting the voltage of the power source to a value causing current to flow through the acid solution for an interval sufficient to clean film from the electrode.

2. The method of claim 1 wherein the acid is at least 2 normal $H_2SO_4$.

3. The method of claim 1 wherein the titanium coated electrode has a surface coating thereon of RuO.

4. The method of claim 1 wherein the surface treatment continues for an interval to remove all film on the exposed surface of the metal electrode.

5. The method of claim 1 wherein the procedure is carried out at ambient temperature and pressure.

6. The method of claim 1 wherein the treated electrode provides consistent response to measurement of NaOCl in NaOH.

7. A method of preconditioning a platinum electrode used in measurement of hypochlorite concentration in basic catholytes, the method comprising the steps of immersing the platinum electrode in an acid bath prior to use, separately placing an oxide coated titanium electrode in the acid bath, and connecting a DC power source between the platinum electrode and the sacrificial electrode wherein the power source is connected such that the negative terminal connected with the platinum electrode, and current flows through the bath between the two electrodes to remove film coating on the platinum electrode.

8. The method of claim 7 including the step of removing an electrode assembly from a measurement gun wherein the electrode assembly is then placed in the acid bath.

9. The method of claim 8 wherein the acid bath is approximately four normal $H_2SO_4$.

10. The method of claim 8 wherein the titanium coated electrode has a surface coating thereon of RuO.

11. The method of claim 8 wherein the surface treatment continues for an interval to remove all film on the exposed surface of the metal electrode.

12. The method of claim 7 wherein the method is conducted at ambient temperature and pressure.

* * * * *